United States Patent [19]

Eibofner

[11] 4,129,945
[45] Dec. 19, 1978

[54] CLAMPING DEVICE FOR DENTAL HANDPIECE

[75] Inventor: Eugen Eibofner, Biberach, Germany

[73] Assignee: Kaltenbach & Voigt GmbH & Co., Biberach, Germany

[21] Appl. No.: 810,990

[22] Filed: Jun. 29, 1977

[30] Foreign Application Priority Data

Apr. 27, 1977 [DE] Fed. Rep. of Germany ....... 2718750

[51] Int. Cl.² .............................................. A61C 1/10
[52] U.S. Cl. .................................... 32/26; 279/1 DC
[58] Field of Search ............ 32/26; 279/1 DA, 1 DC, 279/66, 22, 30, 75, 72

[56] References Cited

U.S. PATENT DOCUMENTS

| 518,175 | 4/1894 | Brooks | 32/26 |
| 848,566 | 3/1907 | Nilsson | 279/72 |
| 2,537,179 | 1/1951 | Albertson et al. | 279/75 |

FOREIGN PATENT DOCUMENTS

| 592225 | 1/1934 | Fed. Rep. of Germany | 32/26 |
| 811250 | 6/1949 | Fed. Rep. of Germany | 32/26 |
| 905528 | 1/1954 | Fed. Rep. of Germany | 32/26 |
| 421875 | 2/1942 | Italy | 32/26 |
| 688136 | 2/1953 | United Kingdom | 32/26 |

Primary Examiner—Russell R. Kinsey
Assistant Examiner—John J. Wilson
Attorney, Agent, or Firm—J. Harold Nissen

[57] ABSTRACT

A clamping device for a dental handpiece to clamp a tooth treatment tool and provide for rapid connection with and disengagement from the dental handpiece. The clamping device includes a pre-clamping element provided with flexible tongues to clamp the shank of the tool prior to clamping the tool shank with the drive shaft of the dental handpiece, and a control mechanism to connect and disconnect the tool shank and the drive shaft.

12 Claims, 3 Drawing Figures

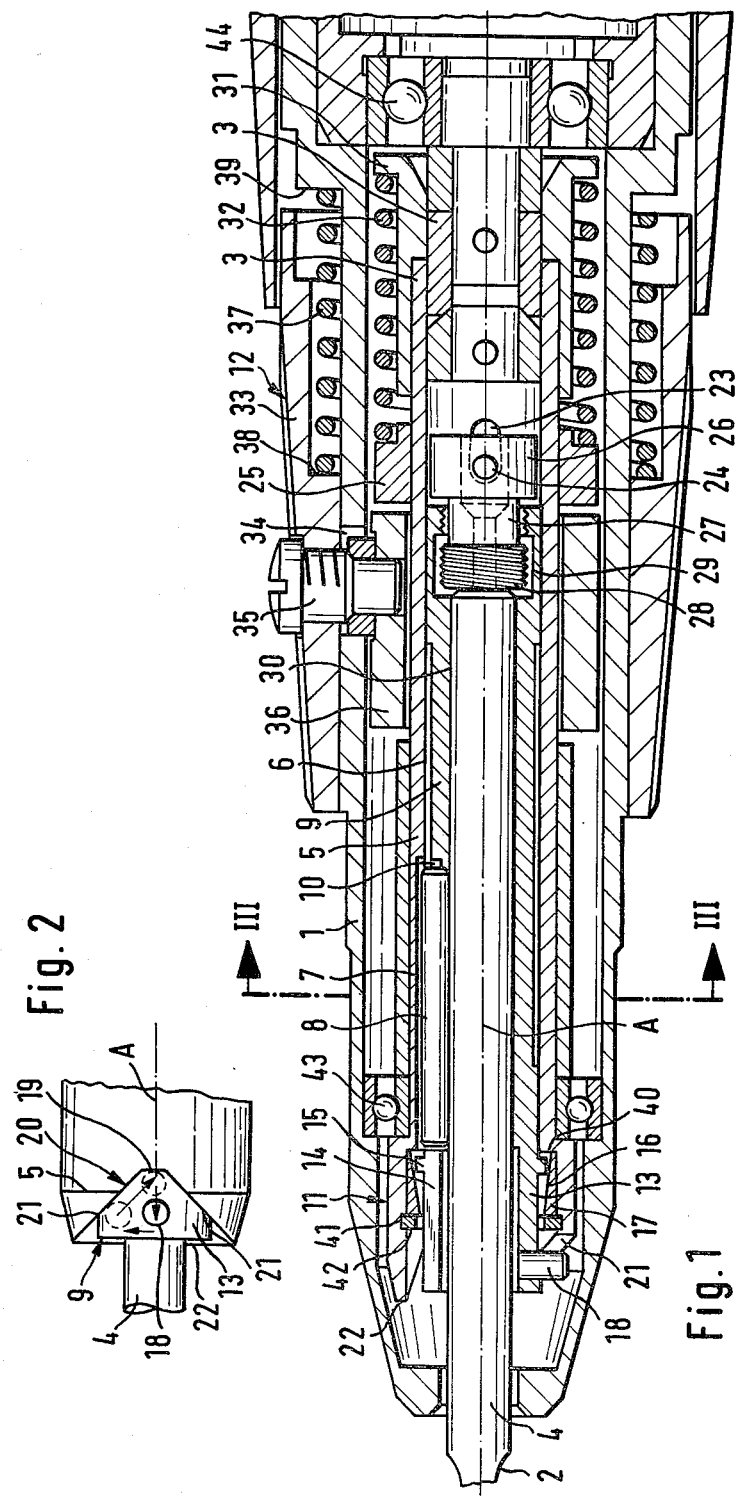

CLAMPING DEVICE FOR DENTAL HANDPIECE

BACKGROUND OF THE INVENTION

This invention relates to a clamping device for dental handpieces.

More particularly, the invention is concerned with dental handpieces having an elongated handpiece sleeve in which a drive shaft is rotatably mounted. The drive shaft drives a tooth treatment tool e.g. a drill. The drive shaft has at one end an opening or hollow portion at its output side to receive the tool shank. The drive shaft at its output side is provided with several depressions distributed over the circumferential wall of the cavity of the end portion, of decreasing depth as viewed in radial section. These depressions are provided for the external suspension of roll bodies which form a roll clamping lock retaining the tool during rotation of the driving shaft. The internal suspension of the roll bodies are formed by openings in a bushing which surrounds the tool shank and is formed in the manner of a roll or antifriction body cage. The openings permit application of or abutment of the roll bodies against the tool shank. The bushing is provided with a pre-clamping element to retain the inserted tool prior to the starting of the rotation of the driving shaft.

In principle, the roll bodies of such self-locking roll clamping locks may be balls. Expediently, however, the roll bodies consist of needles or rollers. The depressions serve for the external suspension for the roll bodies and are designed as axial grooves; and the openings which provide for the internal suspension are axial slots. The depth of the depressions varies in an arcuate fashion, particularly as seen in radial section, and expediently decreases uniformly from the lowest point toward both sides so that the roll bodies occupy their clamping position relative to the tool shank independently of the direction of rotation of the driving shaft when the latter starts up. As a result of a non-uniform decrease of the depth of the depressions a freewheeling can be obtaining in one of the two directions of rotation of the driving shaft. The number of roll bodies or roll elements is generally more than two, preferably three.

The terms used "axial" and "radial" refer to the axes of the driving shaft or respectively to the handpiece sleeve.

A clamping device having the aforesaid features is known from German Pat. No. 811,250. In this known prior art clamping device, a pre-clamping element forming part of a bushing is used to retain or hold the tool prior to the starting of the rotation of the drive shaft. For this purpose, springs are placed around the bushing and act on the roll bodies which consist of needles centrically, i.e. radially inward. A similar arrangement with such springs is disclosed in German Pat. No. 592,225. Upon starting of the drive shaft, the springs constitute a counter-force which act on the roll bodies; the entire control is based upon the proper dimensioning of the springs, and this is usually quite difficult. Accordingly, depending on the dimensioning of the springs, the roll bodies either occupy their clamping position or are prevented from doing so. If the spring force is too weak, the roll bodies are permited to occupy the clamping position, but the roll bodies are prevented from moving out of the clamping position because of the now additionally generated clamping force of the springs. The correct dimensioning of the springs is therefore difficult.

A clamping device similar to the aforementioned type, but without a bushing having a pre-clamping element which surrounds the tool shank, i.e. arranged in the cavity of the driving shaft, is disclosed in German Pat. No. 905,528. In this known clamping device, the pre-clamping element consists of a separate arrangement. In this arrangement, three clamping balls are disposed around the tool shank which are provided in openings in the driving shaft and are arranged in the manner of a ball bearing cage so that they can be applied internally against the tool shank and externally against the conical inner wall of a clamping sleeve in clamped position under the action of a clamping spring and mounted on the driving shaft. By means of an outer grip, the clamping sleeve can be displaced on the driving shaft counter to the action of the clamping spring axially into the release position. In this known clamping device, inwardly pressing the clamping balls may cause damage and deformations on the tool shank which will make repeated use of the tool and its extraction from the clamping device doubtful.

Moreover, all mentioned known clamping devices have the following disadvantages: When a strong load is applied to the tooth treatment tool, i.e. at increased torque, the roll bodies may be wedged between the driving shaft and tool shank so strongly that at decreased torque or standstill of the driving shaft the roll bodies will no longer be able to become released from their clamping position. As a result, the tool cannot be extracted from the clamping device and hence from the handpiece. If, in order to prevent this, the depressions distributed over the inner circumferential wall of the hollow end portion of the driving shaft were formed with a depth decreasing more as seen in radial section, then, difficulties would arise under decreased load at too great a decrease of the depth, the clamping force of the roll bodies would, during the decrease of the load of the tool, i.e. at reduction of the torque, diminish while the driving shaft is still running; or respectively, the roll bodies would release from their clamping position, so that the tool would start to vibrate and become released from the clamping device, and this may lead to dangerous injuries.

It is a principal object underlying the invention to provide a clamping device of the above-mentioned kind to avoid springs difficult to dimension and clamping balls which cause damage to the tool shank, while assurance is given that on the one hand a sufficient clamping action is always exerted by the roll bodies onto the tool shank during the period the driving shaft is running, and that on the other hand the tool can freely be extracted from the clamping device when the driving shaft is stopped and stands still.

SUMMARY OF THE INVENTION

To solve this problem, it is proposed according to the invention that the bushing comprise an axially movable collet. The collet should be axially movable in the cavity of the output side end portion of the driving shaft, and for this purpose an external grip is provided. The external grip is used to move the collet into a clamping and a releasing position, respectively. The collet has radially flexible clamping tongues forming the pre-clamping element, and the tongues are divided from each other by slots originating from the tool-side end of the collet. Each tongue includes an outer radial hump which is applied or abuts against an inclined inner wall of a ring having a wedge-shaped axial section whose inner wall tapers in the direction away from the tool-side end. Each tongue is mounted so that it is fixed against rotary and axial movement and is rotatably and axially undisplaceably in the hollow end portion of the driving shaft. The collet comprises at least one outer radial guide pin which protrudes into a triangular recess disposed in the circumferential wall of the hollow end portion of the driving shaft. The tip of the guide pin is directed in the direction of the axis of the driving shaft, the guide pin being present, when the collet is in the release position as well as in the clamping position of the collet when the driving shaft is stationary. The clamping position of the collet follows the release position, and the pin is in the plane of symmetry of the triangular recess which passes through the axis and the triangle apex; the pin is also further movable into abutment on one of the inclined flanks of the triangular recess while the roll bodies occupy the clamping position; this occurs when the driving shaft starts up, as a result of mutual radial rotation of the collet and driving shaft.

The arrangement of the clamping tongues which are expediently divided from each other by three axial slots, together with the arrangement of the wedge-shaped ring which has its inner wall slanting and associated with the tongues provides for and permits a satisfactory pre-clamping of the tool. This aforesaid arrangement of tongues and slanting wall renders the springs which are difficult to dimension superfluous as well as rendering the damage causing clamping balls superfluous.

The combination of this special pre-clamping element with the at least one radial guide pin and the triangular recess associated therewith makes it possible that the decrease, as viewed in radial section, in the depth of the depressions which are distributed over the inner circumferential wall of the hollow end portion of the spindle sleeve type driving shaft can be selected in such a manner so that after the tool is clamped in the collet and as the driving shaft starts up or starts to rotate, then due to brief mutual rotation between the driving shaft and collet, the roll bodies occupy a sufficient and safe clamping position without the roll bodies unintentionally releasing from their clamping position or clamping condition of the tool as the load of the tool decreases. On the other hand, a control is provided for an intended release of the roll bodies from the clamping position. This occurs automatically upon movement of the outer grip. The outer grip when axially displaced moves the collet to its release position. Such movement of the outer grip casuses the guide pin to interact and cooperate with the inclined flanks of the triangular recess, so that the tool can then freely be removed from the handpiece. Upon the axial displacement of the collet to its release position, which occurs upon actuation of the outer grip so as to move the collet into the release position, the radial humps of the tongues as a result of the aforesaid axial displacement of the collet move out of the cone formed by the inclined surface of the wedge-shaped ring as the tongues become detached from the tool shank. The guide pin in fact slides along the inclined flank of the triangular recess until it is in the apex of the triangle. It is achieved by this arrangement that during said sliding movement of the guide pin the collet necessarily rotates relative to the driving shaft, so that the roll bodies move out of their clamping position and move into to assume their neutral position in the depressions. As the collet returns to the clamping position, the radial humps of the tongues are forced inwardly, so that the tongues pre-clamp the tool shank. As the driving shaft starts up, the roll bodies then occupy their clamping position, as mentioned.

When each clamping tongue as an expedient is provided with an outer radial guide pin, the triangular recess may be designed as a cuneiform notch starting from the output end of the driving shaft.

A particularly favorable form of construction with respect to the interaction of the grip with the collet and the roll bodies consists in that the collet is connected by means of a longitudinal opening in the circumferential wall of the hollow end portion of the driving shaft. This longitudinal opening extends in the direction of the axis and is provided with a sliding socket which is axially movable on the hollow end portion by means of the outer grip. The radial pin and the collet are mutually rotatable while the roll bodies occupy the clamping position.

In order that the invention may be more clearly understood, it will now be described more fully with reference to the accompanying drawings.

BRIEF DESCRIPTION OF THE DRAWINGS

FIG. 1 is an axial section of a dental handpiece taken longitudinally thereof about its longitudinal axis of symmetry illustrating the clamping device of the invention;

FIG. 2 is a detailed left end view of a portion of FIG. 1 with many of the details omitted to show the driving shaft in a position rotated 90° from the position of FIG. 1; and, FIG. 3 is a sectional view taken along line III—III of FIG. 1.

DESCRIPTION OF THE PREFERRED EMBODIMENT

Figure 3:
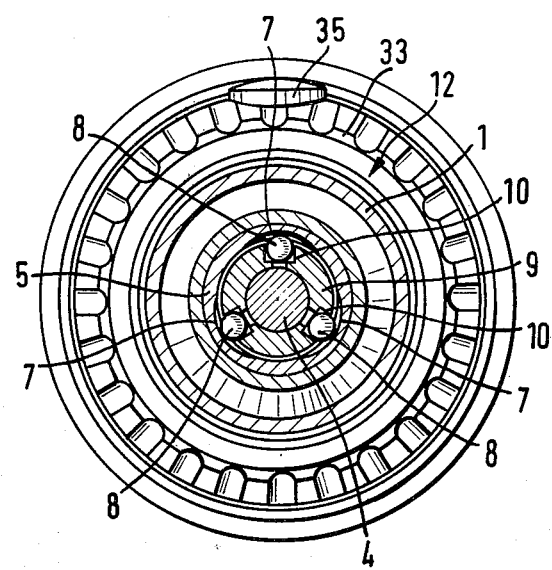

Referring more particularly to FIGS. 1 and 3 of the drawings which show a presently preferred emobdiment of a dental handpiece according to the invention, the handpiece comprises an elongated, substantially cylindrical sleeve 1 having a hollow interior and an outer annual radial projection 39 at one end and a tool opening at the other end. Positioned with the hollow interior of sleeve 1 is a drive shaft 3 rotatably mounted relative to sleeve 1 by means of ball bearings 43 and 44. Both sleeve 1 and drive shaft 3 are concentric about a central longitudinal axis of symmetry A. Drive shaft 3 has a hollow interior and positioned therein and concentric therewith is a bushing in the form of a collet 9 for receiving and holding a tooth treatment tool 2 e.g. a drill having a shank position 4. Connected externally of sleeve 1 and concentric therewith is an external grip 12.

Drive shaft 3 includes a pre-clamping element 11 or a pre-driving clamping section and a driving clamping section generally formed by means of depressions 7 and rollers 8. Pre-clamping element 11 is used to retain the tool 2 within the drive shaft 3 prior to the start up thereof, and rollers 8 are used to hold the tool 2 for rotation with drive shaft 3.

For the uptake of the shank 4, the driving shaft 3 posseses a hollow end portion 5 on the output side. In this end portion, several of the depressions 7 are arranged and distributed over the circumferential wall 6 of the hollow end portion 5. As best seen in FIG. 3, and as viewed in a radial direction and in radial section, the depressions 7 have a depth gradually decreasing from their center to both sides. The depressions 7 serve to hold rollers or roll bodies 8 for the external suspension thereof. Roll bodies 8 form a roll clamping lock retaining the tool 2 as the driving shaft rotates. The internal suspension of the roll bodies 8 is formed by openings 10 in the bushing or collet 9. The openings 10 are dimensioned so that they permit abutment of the roll bodies 8 on the tool shank 4. Inside the bushing 9 is located the shank 4 of a tool 2 inserted in the handpiece, the bushing being designed in the manner of a roll or antifriction body cage.

Shaft 3 has a hollow end portion 5 with an inner circumferential wall 6. Collet 9 is axially displaceable in the hollow end portion 5 of drive shaft 3 by means of an outer or external grip 12 from a clamping postion to a release position and vice-versa. Further, collet 9 is provided with radially flexible clamping tongues 13 which form part of the pre-clamping element 11. Tongues 13 are divided or separated from each other by means of axial slots 14 starting from the left side of FIG. 1 or the tool-side end of the collet 9, and each tongue 13 has an outer radial hump 15. Each hump 15 applies or abuts against an inclined inner wall 16 formed on a ring 17. Ring 17 is wedge-shaped in axial section and tapers in the direction away from the tool-side end in such a way that the radial distance to the inner wall 16 from the axis A of the drive or driving shaft 3 increases. Inner wall 16 of ring 17 has a surface contour in the shape of a truncated cone with the base towards the right being larger than the base towards the left end or towards the tool side. Wedge-shaped ring 17 is rotatable with shaft 3 and is mounted rotatably and axially non-displaceably in the hollow end portion 5 of the driving shaft 3. Collet 9 has three of the tongues 13, and each tongue is provided with an outer radial guide pin 18. Guide pin 18 protrudes into a triangular recess 20 disposed in the circumferential wall 6 of the hollow end portion 5 and points with the tip or triangular apex 19 in the direction of the axis A of the driving shaft 3 away from the left side of FIG. 1 or the tool-side end. The triangular recess 20 is designed, as best seen in FIG. 2, as a cuneiform notch in the circumferential wall 6 starting from the output end 22 of the driving shaft 3.

Pre-clamping element 11 includes an inner enlargement provided at the output end 22 of the hollow end portion 5. This inner enlargement is provided with an annular shoulder 40 and an annular groove 41 in the inner wall of the inner enlargement and a lock ring 42 which is received in the groove 41. Annular shoulder 40 cooperates with lock ring 42 to hold ring 17 for rotation with the drive shaft 3.

In the release position of collet 9 as well as in the following clamping position during standstill of the driving shaft 3, radial guide pin 18 is in the plane of symmetry of the triangular recess 20 which passes through the axis A and the triangle apex 19. The roll bodies 8 assume their clamping position, which occurs as the driving shaft 3 starts up as a consequence of the mutual rotation of collet 9 and driving shaft 3; during this start up, the radial guide pin 18 moves until it abuts against one of the inclined flanks 21 of the triangular recess 20 (see FIG. 2).

As best seen in FIGS. 1 and 2, triangular recess 20 is provided with an inclined flank 21 to permit radial guide pin 18 to move vertically from its center position to its dotted outline position in the direction of the arrow (FIG. 2), and then pin 18 which is shown in dashed outline at its upper position slides along the inclined flank 21 (downwardly and to the right) towards the triangle apex 19 into a second position shown in dashed outline to the right of the position of pin 18 shown in solid outline.

A control mechanism is provided which cooperates with driving shaft 3 and collet 9, and includes a sliding socket 25 connected to collet 9 by means of a pin 24. Circumferential wall 6 of shaft 3 includes a pair of diametrically opposed longitudinal openings 23 to receive the pin 24 and permit guided movement thereof axially along axis A while collet 9 and shaft 3 are rotatable together. Shaft 3 carries a counter bearing 31 in alignment with sliding socket 25 and supports therebetween a helical compression springs 32. External grip 12 includes a slide ring 33 movable along the outer surface of cylindrical sleeve 1. Slide ring 33 has an inner radial projection 38 which cooperates with outer annual projection 39 to hold therebetween a helical compression return spring 37 which surrounds the outer surface of cylindrical sleeve 1.

Collet 9 which is connected by radial pin 24 with sliding socket 25 is axially movable on the hollow end portion 5 by means of the external or outer grip 12. The longidtudinal opening 23 in the circumferential wall 6 extends in the direction of the axis A and permits movement of pin 24 along axis A. The arrangement is such that the radial pin 24 and the collet 9 can rotate mutually while the roll bodies 8 occupy the clamping position. For this purpose, collet 9 is provided with a rotatable axial extension 26 at its end away from the tongues 13. Rotatable axial extension 26 is connected with radial pin 24. Further, the rotatable axial extension 26 has an axial stud 27 protruding into the cavity of the tubular collet 9. Stud 27 is provided with a radial thickening 28. Collet 9 has an inner wall 30 provided with an annular radial recess 29 and radial thickening 28 engages into the annular recess 29.

Spring 32 forces the socket 25 into a first end position corresponding to the clamping position of collet 9. Spring 32 is a compression spring and is designed as a helical spring surrounding the driving shaft 3. The counter-bearing 31 is formed by an outer annual radial projection of the driving shaft 3. This radial projection is farther removed from the output-side end 22 of the driving shaft 3 than the socket 25 in its second end position corresponding to the release position of the collet 9.

Outer or external grip 12 which is formed by sliding ring 33 is axially movable on the hand-piece sleeve 1. Ring 33 is provided with a catch pin 35 protruding through an oblong axial opening 34 in the handpiece sleeve 1 and is in operative connection with sliding socket 25. The catch pin 35 is designed in the form of a screw which is screwed into the wall of sliding ring 33 from the outside and protrudes with its shank through the wall inwardly to engagement with a sliding sleeve 36. The sliding sleeve 36 is arranged on the side of the sliding socket 25 opposite to or to the left of spring 32 and, upon displacement of the sliding ring 33 in FIG. 1 to the right, comes to apply or abut against sliding socket 25, so that socket 25 is also displaced to the right and moves against the force of spring 32.

Return spring 37 holds sliding ring 33 in the position corresponding to the clamping position of collet 9. Also, this return spring 37 is a compression spring and is designed as a helical spring surrounding the handpiece sleeve 1. The return spring 37 is arranged between inner annual radial projection 38 of the sliding ring 33 and outer annular radial projection 39 of the handpiece sleeve 1 and is covered by sliding ring 33.

OPERATION OF THE CLAMPING DEVICE

To open the initially empty collet 9, sliding ring 33 is pushed to the right counter to or against the action of the return spring 37 in FIG. 1. At the same time, sliding socket 25 is pushed to the right by means of catch pin 35 and sliding sleeve 36, counter to or against the force of spring 32, which exerts a restoring action on sliding socket 25. During this displacement to the right, socket 25 moves along the radial pin 24 and the rotatable axial extension 26 to the right. Rotatable extension 26 moves the radial thickening 28 which pulls collet 9 along to the right.

As a result of this movement, humps 15 of the tongues 13 move out of the cone formed by the inclined inner wall 16 of the wedge-shaped ring 17, and the elastic tongues 13 open, moving outwardly, so that the shank 4 of a tooth treatment tool 2 can be introduced or inserted into the collet 9.

Thereafter, sliding ring 33 is released so that it is moved to the left in FIG. 1 under the action of the return spring 37, together with sliding sleeve 36 and catch pin 35. Under the action of spring 32, socket 25 now follows sliding sleeve 36, and because of the elements connected with radial pin 24, axial extension 26, axial stud 27 and thickening 28, and collet 9 are also displaced to the left in the hollow end portion 5 of driving shaft 3. In so doing, humps 15 move into the cone of the wedge-shaped ring 17, and elastic tongues 13 are applied against shank 4 of tool 2 counter to their spring action and pre-clamp shank 4.

Now as driving shaft 3 is set into rotation, there occurs at first a brief relative rotation between driving shaft 3 and collet 9; this relative rotation takes place until roll bodies 8 taken along by the driving shaft 3 are positioned, that is, until the roll bodies 8 have assumed their clamping position between driving shaft 3 and tool shank 4 in the flattening region of the depressions 7, so that tool 2 is fixed as a unit with shaft 3 and rotates upon rotation of the driving shaft 3. During the relative rotation between driving shaft 3 and collet 9, radial guide pin 18 of collet 9 moves out of the plane of symmetry of the triangular recess 20. When pin 18 moves out of the plane of symmetry, it passes through the axis A of the driving shaft 3 (position shown in solid lines in FIG. 2) in radial direction to abutment against one of the two inclined flanks 21 of the triangular recess 20 formed as a wedge-sahped section or notch starting from the output-side end 22 of the driving shaft 3 (upper position shown in broken lines in FIG. 2). While driving shaft 3 stands still, the roll bodies 8 remain in their clamping position, and hence tool shank 4 is in its clamped position.

When tool 2 is to be removed from the handpiece, i.e. from the collet 9, outer grip 12 which includes sliding ring 33 is displaced to the right in FIG. 1, and with such displacement, collet 9 is also displaced axially to the right relative to the driving shaft 3, and the tongues 13 open. At the same time, guide pin 18 slides along the inclined flank 21 of the triangular recess 20 from the upper position shown in broken lines in FIG. 2, into the triangle apex 19, i.e. into the position shown in broken lines appearing to the right of the position shown in solid lines. Thereby, a positive relative rotation of the collet 9 relative to the driving shaft 3 is achieved during the sliding movement of the guide pin 18. During this positive rotation, roll bodies 8 are moved into the lower zone of the depressions 7, so that the roll bodies 8 pass from their clamping position into a neutral position. When the roll bodies 8 are in the neutral position, tooth treatment tool 2 can now be removed from collet 9 without hindrance, and if desired one tool can be exchanged for another.

Ring 17 is rotatably mounted between an annular shoulder 40 of an inner enlargement of the hollow end portion 5 of driving shaft 3 and lock ring 42 provided in annular groove 41 in the inner wall of said enlargement so that the relative rotations between collet 9 and driving shaft 3, occuring as the roll bodies 8 assume and especially as they leave the clamping position, will not be hindered by the clamping effect of the tongues 13 wedged with their humps 15 between the wedge-shaped ring 17 and the tool shank 4.

While there has been described what is considered to be a preferred embodiment of the invention, it will be obvious that various changes and modifications may be mode therein without departing from the scope of the invention.

I claim:

1. In a clamping device for clamping a dental tool to a dental handpiece, said handpiece having an elongated handpiece sleeve containing a drive shaft to drive a tooth treatment tool and having a hollow end portion on the output side to receive the shank of said dental tool, said hollow end portion having inner and outer circumferential walls and having depressions distributed over said inner circumferential wall said depressions being of decreasing depth as viewed in radial section, roll bodies being externally suspended from the interior of said drive shaft at said depressions to form a roll clamping lock retaining the tool during rotation of the drive shaft, a bushing in said hollow end portion of said drive shaft, said bushing having suspension openings to suspend said roll bodies, said suspension openings comprising a roll body or anti-friction cage, said openings permitting application of said roll bodies against the tool shank into a clamping position of said roll bodies, and said bushing including a pre-clamping element into which the shank is inserted for retention thereof prior to commencement of the rotation of said drive shaft, the improvement comprising:

a ring having a wedge-shaped axial section mounted in said hollow end portion of said drive shaft and held thereto against rotational and axial movement relative thereto, said ring including and inclined inner wall which tapers in a direction away from the tool side end; and, said bushing including a collet axially movable in said cavity relative to said drive shaft;

an external grip coupled with said collet for axially moving thereof along a longitudinal axis thereof into tool clamping and release positions;

said collet including at a tool receiving end thereof said pre-clamping element, said pre-clamping element comprising a plurality of radially flexible clamping tongues having slots between each pair of adjacent tongues starting from the tool receiving end of said collet, each of said tongues including an outer radial hump, and at least one outer radial guide pin protruding from said collet into a triangular recess, said pin having a tip pointing in a direction of the longitudinal axis of symmetry of said drive shaft;

said drive shaft having said triangular recess disposed in said circumferential wall of said drive shaft, said triangular recess including a pair of oppositely disposed inclined flanks meeting at a point forming a triangle apex;

said guide pin being movable with said collet to abut one of said inclined flanks of said triangular recess and said roll bodies being moved to their tool shaft clamping position during mutual rotation of said drive shaft and said collet as a unit, and said guide pin engaging one of said inclined flanks when said roll bodies are in their clamping position and being cammed along said inclined flank to said triangle apex when said external grip moves said collet to its release position, and thereby also release said roll bodies from their clamping position.

2. The device according to claim 1, wherein:

each tongue is provided with an outer radial guide pin.

3. The device according to claim 1, wherein:

said triangular recess is formed as a wedge-shaped-notch starting from the output side of said drive shaft.

4. The device according to claim 1, including:

a sliding socket axially movable on said drive shaft;

a radial pin connecting said sliding socket with said collet;

means movably connecting said sliding socket with said external grip for movement of said sliding socket;

said drive shaft having a longitudinal opening in the circumferential wall thereof, said longitudinal opening extending in the direction of said longitudinal axis of said drive shaft, and said radial pin extending through said longitudinal opening for connection of said drive shaft with said sliding socket and said collet; and, said radial pin and said collet being mutually rotatable while said roll bodies occupy the clamping position, and said collet and said sliding socket being axially movable relative to said drive shaft by said external grip.

5. The device according to claim 4, including:

a rotatable axial extension in the interior of said hollow portion of said drive shaft coupled with said collet, said radial pin connecting said axial extension with said sliding socket.

6. The device according to claim 5, including:

an axial stud coupled to said axial extension;

said collet having at the end thereof remote from said tool end a cavity and an annular radial enlargement; and, said stud extending into said cavity and having a radial thickening which extends into said annular enlargement.

7. The device according to claim 4, including:

a counterbearing cooperating with said sliding socket fixed to said drive shaft;

a spring positioned on said drive shaft and held between said counter bearing and said sliding socket urging said sliding socket into a first end position corresponding to the clamping position of said collet.

8. The device according to claim 7, wherein:

said spring is a compression spring formed as a helical spring surrounding the driving shaft and, said counter-bearing including an outer annular radial projection of the drive shaft, which projection is farther removed from the output end of said drive shaft than said socket in its second end position corresponding to the release position of said collet.

9. The device according to claim 4, wherein:

said outer grip includes a slide ring axially movable on said handpiece sleeve, said slide ring includes a catch pin which protrudes through an axial opening in said handpiece sleeve and is operatively connected with said socket.

10. The device according to claim 9, including:

a sliding sleeve axially movable along said drive shaft adjacent to said sliding socket and applied thereto; and, said catch pin connecting said sliding sleeve with said slide ring.

11. The device according to claim 9, including:

a return spring holding said sliding ring in the position corresponding to the clamping position of said collet.

12. The device according to claim 11, wherein:

said return spring is a compression spring designed as a helical spring surrounding the handpiece sleeve; and, including:

an inner annular radial projection on said sliding ring and an outer annular radial projection extending from said handpiece sleeve, said return spring being held between said inner annular radial projection and said outer annular radial projection; and, said slide ring covering said return spring.

* * * * *